| United States Patent [19] | [11] | 4,178,211 |
|---|---|---|
| Leavitt | [45] | Dec. 11, 1979 |

[54] PROCESS FOR PRODUCING CITRIC ACID

[75] Inventor: Richard I. Leavitt, Baton Rouge, La.

[73] Assignee: Ethyl Corporation, Richmond, Va.

[21] Appl. No.: 910,359

[22] Filed: May 30, 1978

Related U.S. Application Data

[63] Continuation-in-part of Ser. No. 773,976, Mar. 3, 1977, abandoned.

[51] Int. Cl.$^2$ .............................................. C12D 1/04
[52] U.S. Cl. ...................................... 195/30; 195/37
[58] Field of Search ......................... 195/30, 37, 28 R

[56] References Cited

U.S. PATENT DOCUMENTS

| 3,809,611 | 5/1974 | Takayama et al. | 195/30 |
| 3,873,424 | 3/1975 | Kimura | 195/28 R |
| 3,926,724 | 12/1975 | Takayama et al. | 195/28 R |
| 3,966,553 | 6/1976 | Charpentier et al. | 195/28 R |
| 3,996,106 | 12/1976 | Maldonado et al. | 195/30 |

FOREIGN PATENT DOCUMENTS 1359097  7/1974  United Kingdom .
1359632  7/1974  United Kingdom .

*Primary Examiner*—Lionel M. Shapiro
*Attorney, Agent, or Firm*—Donald L. Johnson; John F. Sieberth; James M. Pelton

[57] ABSTRACT

A process for producing citric acid by fermentation employing the species *Candida lipolytica* and using a mixed carbon source as the nutrient medium in which a carbohydrate is used as a fermentation initiator and an organic acid or salt thereof is used as the primary nutrient medium so that a high ratio of citric to isocitric acid is produced and maximum productivity maintained.

8 Claims, No Drawings

PROCESS FOR PRODUCING CITRIC ACID

CROSS REFERENCE TO RELATED APPLICATION

This application is a continuation-in-part of application Ser. No. 773,976, filed Mar. 3, 1977, now abandoned.

BACKGROUND OF THE INVENTION

This invention relates to a process for producing citric acid by fermentation.

Citric acid is widely used in the food and pharmaceutical industry as, for example, an acidulant in beverages or in the preparation of jams. Citric acid is also used as an antioxidant or as a stabilizer in various food products. More recently, citric acid has been employed in various detergent compositions as a detergent builder.

Hitherto citric acid has been produced from carbohydrates such as molasses by culturing moulds. Recently, it has been reported that certain strains of the genus Candida, namely *Candida subtropicalis* and *Candida fibrae*, produced citric acid from various assimilable carbon sources, such as carbohydrates, alcohols, organic acids, n-alkanes, glycerides and other fats or oils, and also crude materials containing these carbon sources, when aerobically cultured in an aqueous medium. It has also been reported that species of Candida will produce citric acid from mixtures of acetate and glucose, however, both the ratio of citric acid to isocitric acid and the yields were too low to be of commercial significance. As far as is heretofore known, no yeast has been separated which produces citric acid from acetic acid in the presence of a small amount of glucose in mineral salts media at both high yield and citric to isocitric acid ratio.

When citric acid is produced using yeast, such as from the genus Candida, usually a considerable amount of isocitric acid occurs in the culture medium as a by-product. Isocitric acid is an organic acid for which there is not a significant amount of commercial use. Thus, it is rarely desired to produce isocitric acid. Moreover, the by-production of isocitric acid makes isolation and purification of citric acid in the culture medium very complicated. Accordingly, the present invention is concerned with the suppression of by-product isocitric acid in the fermentation process while maintaining the production of citric acid in a yield equal to or greater than that of the same process in which the by-production of isocitric acid is not suppressed. Moreover, the present invention is concerned with increasing the yield of citric acid over previously known processes in such a manner that a commercially feasible process is obtained which is competitive with other sources of assimilable carbon.

DESCRIPTION OF THE INVENTION

In accord with the above objectives, my invention provides a process for producing citric acid which comprises aerobically fermenting a mixed carbon source nutrient medium in a submerged culture of *Candida lipolytica*, ATCC-20510, said process being further characterized in that said mixed carbon source is a mixture of a carbohydrate and a straight chain monocarboxylic acid or salt thereof having from 2 to about 20 carbon atoms, the fermentation liquor having an initial concentration of from about 1 to about 5 percent by weight of said monocarboxylic acid or salt thereof and, as a fermentation initiator, from 0.5 to about 2.5 percent by weight of said carbohydrate with no further addition of said carbohydrate to the fermentation mixture and a total of from about 10 to about 20 percent by weight of said monocarboxylic acid or salt thereof being added over the total fermentation period of from about 1 to about 15 days whereby said process produces a ratio of citric to isocitric acid of at least 4:1, respectively. Preferably, the carbon source is a lower organic acid or salt thereof such as those having from 2 to about 6 carbon atoms. The most preferred carboxylic acid is acetic acid because of its wide availability and low cost. The initiating carbohydrate is preferably a monosaccharide, such as glucose.

The microorganism employed in my invention is a member of the genus Candida and a stable mutant of the species *Candida lipolytica*, ATCC-8661. It has been found that this organism produces species of a different colonial and microscopic morphology detectable in plate cultures 48 hours or more old. This variant is distinguished by a smooth textured colonial surface, is stable in that it does not revert to stock type after repeated transfer, breeds true while the parent does not and produces levels of total "citric" acid from acetate equal to or higher than its parent. It should be noted that, as used throughout this specification, the term "citric" refers to both true citric acid plus isocitric acid. In other respects, the taxonomy of this variant, sometimes designated herein *Candida lipolytica* ATCC-8661 Var.s, is similar to its parent. This variant has been deposited with the American Type Culture Collection and given access No. ATCC-20510, which will be used to designate this variety hereafter.

The carbon source employed in my process can be a monocarboxylic acid. Other carbon sources have been used with microorganisms of the genus Candida, but require other additives, such as an additional amount of iron, or other specific conditions to obtain high yields and higher ratios of citric to isocitric acid. In my process, the monocarboxylic acid can be a straight chain monocarboxylic acid. Typical of such straight chain monocarboxylic acids are acetic, butyric, hexanoic, octanoic, decanoic, lauric, myristic, palmitic, stearic and arachidic acid. Thus, the carboxylic acid used as a carbon source in my process is preferably a straight chain, even-numbered monocarboxylic acid having from 2 to about 20 carbon atoms. Even more preferred are such acids having from 2 to about 6 carbon atoms. Most preferred is acetic acid since it requires no breakdown of the longer carbon chain in order to form the citric acid molecular structure and it is widely available at low cost.

The aqueous culture medium employed in the present invention contains assimilable carbon sources, assimilable nitrogen sources, inorganic salts, and, if necessary, organic minor nutrients.

Sources of assimilable carbon are the organic acids as described above. However, I have found that an "initiator" or adjuvant for the production of citric acid can be used to enhance the initial growth rate of the microorganism and yield of citric acid both initially and over the entire fermentation process period. Typical of such an "initiator" is a carbohydrate. Examples of carbohydrates which can be employed in my invention are glucose, galactose, saccharose, fructose, sucrose and the like. Preferably, glucose is employed as the initiator, again because of its low cost and availability.

Suitable examples of nitrogen sources include organic or inorganic ammonium salts, gaseous ammonia, aqueous ammonia, amino acids, and other conventional nitrogen sources.

Inorganic salts employed in the nutrient medium are entirely conventional and include, for example, the phosphate, sulphate or chloride of potassium, sodium, magnesium, ferrous or ferric iron, or manganese.

As minor organic nutrients which can be employed in my process, there can be mentioned, as examples, yeast extract, malt extract, corn steep liquor, peptone, beef extract, soybean hydrolysate, casein hydrolysate, or other crude materials containing organic minor nutrients.

Fermentation is carried out aerobically. Usually, fermentation is allowed to proceed for 1 to about 10 days at a temperature of from about 24° to about 37° C. The pH of the medium is usually maintained in a range of 5 to 9 by addition of alkali or acids, as appropriate.

In accord with the process of my invention, the amount of carbohydrate used as an "initiator" or activator for *Candida lipolytica* can range from about 0.5 to about 2.5 percent by weight of the fermentation liquor. At amounts less than this the influence of the carbohydrate is negligible and at amounts greater than this only the expected growth and citric acid production associated with conventional processes occurs. Further, the initial amount of carboxylic acid or salt thereof can range from about 1 to about 5 percent by weight of the fermentation liquor. This initial amount of the primary carbon source is preferably supplemented periodically during fermentation up to a total of from about 5 to about 20 percent by weight of the fermentation liquor over the entire period. Preferably, the initial concentration of the carbohydrate initiator can range from about 1 to about 2 percent by weight and the total monocarboxylic acid or salt thereof can range from about 10 to about 15 weight percent added to the fermentation liquor.

The citric acid accumulated in the fermentation liquor can be recovered by conventional methods; for example, after removing cells by centrifuging or filtration, citric acid is separated by ion exchange from the filtrate; or the filtrate is concentrated, and calcium citrate is obtained from the concentrated filtrate after adding calcium hydroxide.

The following examples will serve to illustrate various aspects of my invention. As used herein, all percentages are by weight, unless otherwise stated.

EXAMPLE 1

This example illustrates the qualitative growth response of *Candida lipolytica* over various other known citric acid and food grade yeast producers. In each instance, a nutrient medium consisting of MgSO$_4$.7H$_2$O—0.5 g/liter
NH$_4$Cl—1.0
KH$_2$PO$_4$—1.0
Yeast extract—0.25 was supplemented with 0.2% of glucose, methanol, ethanol or sodium acetate, solidified with the addition of 1.5% agar and used to support growth of (a) *Aspergillus niger* ATCC-1015—parent strain of fungus known as a citric acid producer from carbohydrates, (b) *Candida lipolytica* ATCC-8661—a yeast used to produce citric acid from hydrocarbons, (c) *Candida tropicalis* ATCC-1369—a food grade yeast, and (d) *Candida utilis* ATCC-9950—a food grade yeast.

The growth response was determined after overnight incubation on a relative basis for comparison between the different organisms and with no attempt to optimize growth of each species. The results are shown in the following table:

Table 1

| | Growth Response of Various Microorganisms on Agar Plates Containing Nutrient Media | | | |
|---|---|---|---|---|
| Carbon Source | *Aspergillus niger* | *Candida utilis* | *Candida tropicalis* | *Candida lipolytica* |
| None | +1 | +2 | +2 | +3 |
| Glucose | +5 | +6 | +5 | +6 |
| Acetate | +3 | +5 | +5 | +6 |
| Ethanol | +1 | +5 | +5 | +5 |
| Methanol | +1 | +2 | +2 | +3 |

All three Candida species grow well on either glucose, acetate or ethanol. None of the species responded to methanol. The most surprising aspect of this is the good growth response of *Candida lipolytica* on both glucose and acetate, as well or better than any other growth response shown.

These qualitative experiments were followed by comparison of citric acid production between *Candida utilis* and *Candida lipolytica* in submerged shake flask cultures.

EXAMPLE 2

The microorganisms listed in Table 2 below were grown in the mineral salts medium described in Example 1 supplemented with trace metal thiamine, 8% calcium carbonate and with 5% of either glucose, n-tetradecane, sodium acetate or 3% ethanol added to the flasks. The cultures were shaken at room temperature and examined for the presence of "citric" acids (includes both citric and isocitric acids) after 92 hours. The results in mg/liter are shown in Table 2:

Table 2

| | "Citric" Acids Produced From Various Carbon Sources | | | |
|---|---|---|---|---|
| Microorganisms | Ethanol | Acetate | Glucose | n-Tetradecane |
| *Candida lipolytica* | 1866 | 324 | 19,806 | 20,712 |
| *Candida utilis* | 146 | 10 | 100 | 0 |

These results show that *Candida lipolytica* is a preferred microorganism for production of "citric" acids and shows carbohydrates and paraffins are preferred carbon sources. This result differs from the qualitative results of Example 1 which indicated that acetate was equivalent to carbohydrates but indicates that differences in media employed, inocula preparation and culture conditions affect parameters which enter into the production of citric acid. The effect of such differences requires understanding before the process is finalized.

EXAMPLE 3

This example illustrates the surprising results obtained using a preferred embodiment of my invention. In this example, a spontaneous, stable nutrient of the organism previously used, *Candida lipolytica* ATCC 8661, now designated ATCC-20510, was employed with a combination of a carbohydrate activator and acetate as the primary carbon source. This mutant was found to produce higher levels of citric acid from acetate than the organism designated 8661 and is described hereinabove. Its designation in the American Type Culture Collection is 20510. Two sources of inocula were employed. In the first, the mineral salts supplemented with yeast extract of Example 1, plus additional $NH_4Cl$—2.0 g/liter, $CaCl_2$—10 g/liter, $MgCl_2.5H_2O$—0.5 g/liter and deleting the $MgSO_4$, was prepared. In the second, cells were grown for 17 hours in yeast-maltose media consisting of 0.3% yeast extract, 0.3% maltose extract, 0.5% peptone and 1% glucose. One ml of each inoculum was added to 25 ml of mineral salts-yeast extract media containing 1.0% sodium acetate. After 24 hours inoculation with shaking at 25° C., an additional 2% sodium acetate was added to the cultures. The cultures were shaken for an additional 4 days and the amount of "citric" acid formed was determined. The results are shown in Table 3:

Table 3

"Citrate" Production by *Candida lipolytica* ATCC 20510 From Acetate Using Various Inoculum

| Inoculum | "Citrate" mg/ml |
|---|---|
| Mineral salts media culture | 3.13 |
| Yeast-maltose (YM) media culture | 8.41 |

EXAMPLE 4

The ratio of citric to isocitric acid was determined using NMR analysis of the fermentation broth containing citric acid produced from a hydrocarbon, such as n-tetradecane, and comparing the ratio of citric to isocitric acids produced by different organisms, i.e., *Candida lipolytica* ATCC-8661 and *Candida zeylanoides* KY-6161, with the result shown in Table 4. Also shown in Table 4 is the comparative ratio of citric to isocitric acid using *Candida lipolytica* ATCC-8661 when fermented with different carbon sources.

Table 4

Ratio of Citric Acid to Isocitric Acid Using Various Microorganisms and Carbon Sources

| Organisms | Citric, mg/ml | Isocitric, mg/ml | Ratio of Citric/isocitric |
|---|---|---|---|
| Hydrocarbon | | | |
| *Candida zeylanoides* KY-6161 | 56.2 | 50.5 | 1.11 |
| *Candida lipolytica* ATCC-8661 | 25.0 | 8.2 | 3.05 |
| | 2.5 | 0.82 | 3.05 |
| Acetate | | | |
| | 1.56 | 0.34 | 4.50 |

Although the absolute amounts of the total acid produced was less than the maximum reported in the literature, the ratio of citric to isocitric acid was much higher with *Candida lipolytica* and with acetate. Optimization of yields and growth as shown below, according to the process of my invention, allows advantageour recovery of high amounts of citric acid.

As a preferred embodiment of my invention, it has been found that citric acid produced from a vigorous inocula prepared from yeast-maltose broth supplemented with 5 weight percent sodium acetate grown for 24 hours and then added as a 5 weight percent inoculum to a mineral salts media also containing 2 weight percent sodium acetate, 1 weight percent glucose and 0.25 weight percent yeast extract. The culture is shaken for 24 hours after which an additional 4 weight percent sodium acetate is added, then after 48 hours an additional 4 weight percent sodium acetate is added. Finally, after 72 hours from the last addition another 5 weight percent of sodium acetate can be added so that a total of 15 weight percent sodium acetate has been added since the initial 24-hour inoculum was started with glucose and sodium acetate over a total period of 6 days or more. The details and results are given in the following example.

EXAMPLE 5

A 12-day fermentation using *Candida lipolytica* ATCC-20510 was conducted using cells grown for 24 hours at room temperature in a yeast-maltose media containing 0.3 weight percent yeast extract, 0.3 weight percent maltose extract, 0.5 weight percent peptone, 1 weight percent glucose and 5 weight percent sodium acetate. After this initial 24-hour growth period, a 5 weight percent inoculum from this culture is added to a mineral salts media as in Example 4 containing 2 weight percent sodium acetate, 1 weight percent glucose and 0.25 weight percent yeast extract. Solid sodium acetate was added after 24 hours, 48 hours and 120 hours from inoculation. After 12 days "citric" acids had reached a concentration of 5.13 weight percent. The maximum rate of "citric" acids production was 10.1 g/liter/day.

EXAMPLE 6

In a 7-liter stirred tank fermenter, there was added 3 liters of an aqueous solution containing $MgSO_4.7H_2O$—1.0 g/liter
$NH_4CL$—6.0
$KH_2PO_4$—2.0
Yeast extract—0.5

To this solution was then added 2% by weight of glucose and 4 weight percent of sodium acetate. The temperature was controlled at 30° C., the pH at 7.2, and the stirrer set at 1000 rpm. The air rate through the fermentation tank was 2000 cc/min. Then 225 ml of a 24-hour inoculum of *Candida lipolytica* ATCC-20510 was added and allowed to run for 24 hours. At this time, and subsequently every 24 to 36 hours, additional acetate was added to a total level of 12 weight percent. At the end of six days, there was produced 8 weight percent of citric acid. The maximum rate of production of citric acid during this run was over a period of 48 hours in which 2.1 weight percent of citric acid was produced every 24 hours.

EXAMPLE 7

This example illustrates the production of citric acid in a continuous process. In the continuous process, it was found that high productivity could be maintained by doubling the amounts of salts described in Example 1. In addition to mineral salts, the media contained 4% sodium acetate and 2% glucose at the time of inoculation. The inoculum consisted of 225 ml of an 18-hour culture of *Candida lipolytica* ATCC-20510 grown in yeast maltose broth supplemented with 5% sodium acetate. The fermentation was conducted in continuous operation with media pumping into the fermenter at the rate of 405 ml per 24 hours. The imput media contained 30% sodium acetate, 1.5% glucose and 5 x mineral salts. In addition, 210 ml of 50% acetic acid were required every 24 hours to maintain the pH of the culture at 7.2.

During this run, the citric acid level was maintained at 128 mg/ml with a productivity of 30 mg/ml/day.

From the foregoing description of my invention, one skilled in the art can envision numerous variations in conditions, concentrations, organisms, procedures, etc., which are within the scope of my invention. It is, therefore, desired that my invention be limited only by the lawful scope of the following claims.

What is claimed is:

1. A process for producing citric acid which comprises aerobically fermenting a mixed carbon source nutrient medium in a submerged culture of *Candida lipolytica*, ATCC-20510, said process being further characterized in that said mixed carbon source is a mixture of a carbohydrate and acetic acid or salt thereof with the fermentation liquor having an initial concentration of from about 1 to about 5 percent by weight of said acetic acid or salt thereof and, as a fermentation initiator, from 0.5 to about 2.5 percent by weight of said carbohydrate with no further addition of said carbohydrate to the fermentation mixture and a total of from about 5 to about 20 percent by weight of said acetic acid or salt thereof being added over the total fermentation period of from about 1 to about 15 days whereby said process produces a weight ratio of citric to isocitric acid of at least 4:1, respectively.

2. The process of claim 1 wherein said acetic acid or salt thereof is sodium acetate.

3. The process of claim 1 wherein said carbohydrate is glucose.

4. The process of claim 1 wherein said acetic acid or salt thereof is sodium acetate and said carbohydrate is glucose.

5. The process of claim 1 wherein initial concentration of said carbohydrate is from 1 to about 2 percent by weight and a total of from about 10 to about 15 percent by weight of said acetic acid or salt thereof is added to the fermentation liquor.

6. The process of claim 1 wherein said process is carried out at from about 20° to about 40° C. at a pH of from about 5 to about 9 for 1 to about 10 days with agitation using a nutrient medium containing mineral salts and a yeast-maltose broth.

7. The process of claim 1 in which said acetic acid or salt thereof is sodium acetate and said sodium acetate is added during the first one to six days of fermentation.

8. The process of claim 1 wherein said carbohydrate is glucose, said acetic acid or salt thereof is sodium acetate and the initial concentration of said glucose is from 1 to about 2 percent by weight and a total of from about 10 to about 15 percent by weight of said sodium acetate is added to the fermentation liquor.

* * * * *